United States Patent
Norwood et al.

(10) Patent No.: US 7,906,623 B2
(45) Date of Patent: Mar. 15, 2011

(54) DEFATTING COLLAGEN

(75) Inventors: Derek Samuel David Norwood, Irvine (GB); Robert Gordon Paul, Thornhill (GB)

(73) Assignee: Devro PLC (GB)

( * ) Notice: Subject to any disclaimer, the term of this patent is extended or adjusted under 35 U.S.C. 154(b) by 12 days.

(21) Appl. No.: 12/158,432

(22) PCT Filed: Dec. 22, 2006

(86) PCT No.: PCT/GB2006/004932
§ 371 (c)(1),
(2), (4) Date: Oct. 7, 2008

(87) PCT Pub. No.: WO2007/072064
PCT Pub. Date: Jun. 28, 2007

(65) Prior Publication Data
US 2009/0023899 A1    Jan. 22, 2009

(30) Foreign Application Priority Data
Dec. 23, 2005    (GB) .................................. 0526347.0

(51) Int. Cl.
*A61K 38/17*    (2006.01)
(52) U.S. Cl. ...................................................... 530/356
(58) Field of Classification Search .................... 530/356
See application file for complete search history.

(56) References Cited

U.S. PATENT DOCUMENTS

| 4,285,986 A | 8/1981 | Cioca et al. |
| 6,092,301 A | 7/2000 | Komanowsky |

FOREIGN PATENT DOCUMENTS

| GB | 1361540 | 7/1974 |
| WO | WO 03/017770 A1 | 3/2003 |
| WO | WO 2004/073407 A1 | 9/2004 |

OTHER PUBLICATIONS

Machine translation of ES 2 238 926 (Sep. 1, 2005—cited on IDS).*
International Search Report corresponding to International Application No. PCT/GB2008/004932 mailed Nov. 26, 2007.

* cited by examiner

*Primary Examiner* — Suzanne M. Noakes
(74) *Attorney, Agent, or Firm* — Myers Bigel Sibley & Sajovec, PA

(57) ABSTRACT

Pig rind is one source of collagen for processing into products, such as sausage casings and films. However, it has a high fat content. The invention produces a defatted collagen paste from a collagen source by cutting the collagen into pieces, pressurising the collagen pieces to squeeze out fat and disintegrating the defatted pieces to form a fibrous paste. The paste can be used to produce a gel, which may be extruded to produce a collagen product.

19 Claims, 1 Drawing Sheet

DEFATTING COLLAGEN

CROSS-REFERENCE TO RELATED APPLICATIONS

This application is a 35 U.S.C. §371 national phase application of PCT Application No. PCT/GB2006/004932, filed on Dec. 22, 2006, which claims priority from Great Britain Application Serial No. GB 0526347.0, filed on Dec. 23, 2005, the disclosures and contents of which are incorporated by reference herein in their entireties. The above-referenced PCT International Application was published in the English language as International Publication No. WO 2007/072064.

BACKGROUND OF THE INVENTION

The present invention relates to a method of making a paste for the production of collagen gel from natural skins, particularly from a porcine collagen source. In particular, it relates to the treatment of pig rind, fat removal therefrom and production of a collagen gel suitable for processing into collagen products, such as casings and films.

SUMMARY OF THE INVENTION

Artificial collagen products, such as films and sausage casings, made from reconstituted collagen derived from natural animal sources have been commercially available for many years. Collagen films are typically used for wrapping food products, such as hams etc. Collagen casings are typically filled with meat mixture to produce sausages. At present, the principal source of animal collagen is bovine collagen derived from the hides of cattle. After the cattle have been slaughtered, the hides are removed together with the underlying collagen layer. Usually, the hide is then treated with lime to swell the collagen. The collagen layer is then mechanically separated from the hide to form a "split", minced and processed into a collagen gel in known manner.

Collagen is also potentially available from a number of other sources, such as the skins of pigs, sheep, goats, birds, fish etc., but none of these have found widespread commercial use up to the present time.

Natural collagen is available from pigs either as pulled pigskins or more commonly as so-called "rind". Pulled pigskins are produced by flaying a whole or substantially whole skin from the body of the pig, usually a sow. These are hairy hides of a traditional type and may be treated with salt to preserve them and facilitate further processing. Such pigskins can be processed similarly to bovine splits. Rind is smaller pieces, typically about A4 paper size, which are cut from joints after the pig (usually a young pig) has been cut up. Obviously, the size and shape of the rind pieces depend on the joint from which they are cut. Typically, they are removed together with a substantial amount of fat.

Our prior patent publications WO03/017770 and WO04/073407 relate to the problems encountered in the production of artificial collagen products from porcine collagen derived from pigs. A particular problem with porcine collagen is that it has a relatively high fat content, which, if not reduced, results in collagen products having inferior mechanical properties. It has been found difficult to mechanically separate the fat from the collagen, since the fat and collagen layers are not neatly stratified in the natural pigskin, but the collagen layer tends to include inclusions of fat around the bristles. Therefore, in contrast to bovine collagen, it is not usually satisfactory to simply separate the collagen from the fat content in pigskin by cutting away the subcutaneous fatty layer in a defleshing machine.

Patent publication WO03/01770 describes the defatting of young porcine raw material and also the defatting of sow skins. Generally, this is achieved by a combination of mechanical separation and additional fat removal steps. In both cases, the pigskins are subject to a mechanical separation of the fat and collagen layers in a defleshing machine.

Patent publication WO04/073407 describes a similar defatting procedure carried out on sow skins only.

However, there are problems in removal of fat from porcine collagen in the manner described in these patent specifications. Firstly, the pigskins are normally subject to an alkaline treatment (using sodium carbonate or sodium hydroxide) which swells the collagen. This expands the collagen layer and facilitates separation of the fatty layer from the hide and collagen layer in the defleshing machine. The separated pigskin, may also be subjected to a further strong alkali treatment to remove hair and bristles from the collagen. Such alkaline treatment is found to degrade the collagen and detracts from the mechanical properties of the collagen products produced. Furthermore, a neutralisation step is usually required to neutralise the alkali.

U.S. Pat. Nos. 6,482,240 and 7,022,358 describe the reduction of fat content by enzymic defatting of porcine rinds.

A further problem relates to the availability of pigskins. The majority of the examples in the abovementioned patent publications relate to the treatment of sow hides. Sows are female pigs about one year old or more, who have generally borne a litter. However, the vast majority of pigs (typically around 90%) are young pigs which are killed for meat at around four months old. Typically, sows make up only a small proportion of the total pig population at any given time. Therefore, there is only a limited source of sow skins. On the other hand, sow skins, being much larger in size, are more suitable for the mechanical removal of the fatty layer in a defleshing machine. Generally, skins from young pigs killed at around four months are only available in pieces the size of A4 paper sheets (known as "rind") and are therefore much less suitable for treatment in a defleshing machine.

A further problem is that pigskin is generally processed at a leather tannery, particularly in the case of sow skins. This may cause complications as regards health regulations, since such tanneries are not generally operated under conditions appropriate for food processing.

It is therefore an object of the present invention to provide a process for the removal of fat from a source of natural collagen, particularly porcine collagen, which mitigates these problems and is in particular suitable for the defatting of relatively small pieces of raw material.

Generally speaking, the present invention cuts the natural collagen into pieces and then the fat is removed from the collagen pieces by squeezing out the fat under pressure.

Specifically, the invention provides a process for the production of a defatted collagen paste, which comprises:
  providing natural collagen from animal, mammalian, avian or fish skin;
  cutting the collagen into pieces;
  subjecting the collagen pieces to pressure to squeeze out fat and produce defatted pieces; and
  disintegrating the defatted pieces to form a fibrous paste.
The present invention is in principal applicable to the production of a collagen paste from a wide variety of animal, mammalian, avian and fish sources; such as sheep (lambs and ewes), goats, birds (chickens, turkeys etc.) and fish (e.g.

salmon skins). However, the present process is particularly adapted for the processing of pig rind which has a high fat content.

It is to be understood that typically the ratio of collagen to fat in natural pigskins is in the region 1:1 to 1.5:1. In rinds the ratio is 1:1 to 1:5 typically.

The structural characteristics of pigskins are well known and are discussed for example in World Leather, October, 1997, page 85-90. Thus, pigskin is known to comprise from outside to inside an epidermis layer, dermis layer and subcutaneous fatty layer. The dermis layer is relatively thick compared to the epidermis and is a principal location of collagen fibres. The big bristles are also located in the dermis layer and "cones" of fat tend to extend upwardly from the subcutaneous fatty layer through the dermis layer at the base of each bristle follicle. Thus, there tends to be a division between the collagen-containing dermis layer and the subcutaneous fatty layer. This division is less pronounced in younger pigs and more pronounced in older pigs.

In the prior art, one of the most effective ways of increasing the ratio of collagen to fat is to carefully control the mechanical treatment of the pigskins in the tannery. The fresh pigskins can be subjected to mechanical defleshing which removes the subcutaneous fatty layer and some of the dermis layer to an extent that the ratio of collagen to fat is in the required ratio. However, as mentioned above, removal of fat by mechanical defleshing is difficult to carry out on the A4-sized rinds widely available from young pigs. The present invention avoids this problem by cutting the rind (epidermis, dermis and subcutaneous fatty layer) into pieces and then squeezing out fat to increase the collagen to fat ratio.

In another aspect of the invention, the percentage of fat in the porcine collagen product is reduced to a level below 20%, particularly below 18% and especially below 16% by weight on a dry weight basis.

The ratio of collagen to fat is at least 2.5:1, preferably at least 3, particularly at least 3.5 and especially at least 4:1. Higher ratios of collagen to fat above 10:1, and even above 20:1 may be achieved. Preferably, the ratio is above 30:1 and especially above 40:1. However, the fat content is preferably controlled to achieve a good overall balance of properties in the final collagen product. Preferred ranges include 25:1 to 50:1, particularly 30:1 to 45:1. Thus, a certain proportion of fat in the final product improves the appearance thereof, giving it an attractive sheen, and where the product is a film to be used around cooked products, tends to improve the cooking properties of the film. The unsaturated nature of the pig fat may provide unexpected strength (e.g. via cross-linking). Thus, the amounts of other additives, such as glycerol or other humectants, included in the product may depend to an extent on the proportion of fat.

DETAILED DESCRIPTION OF THE INVENTION

Figure 1:
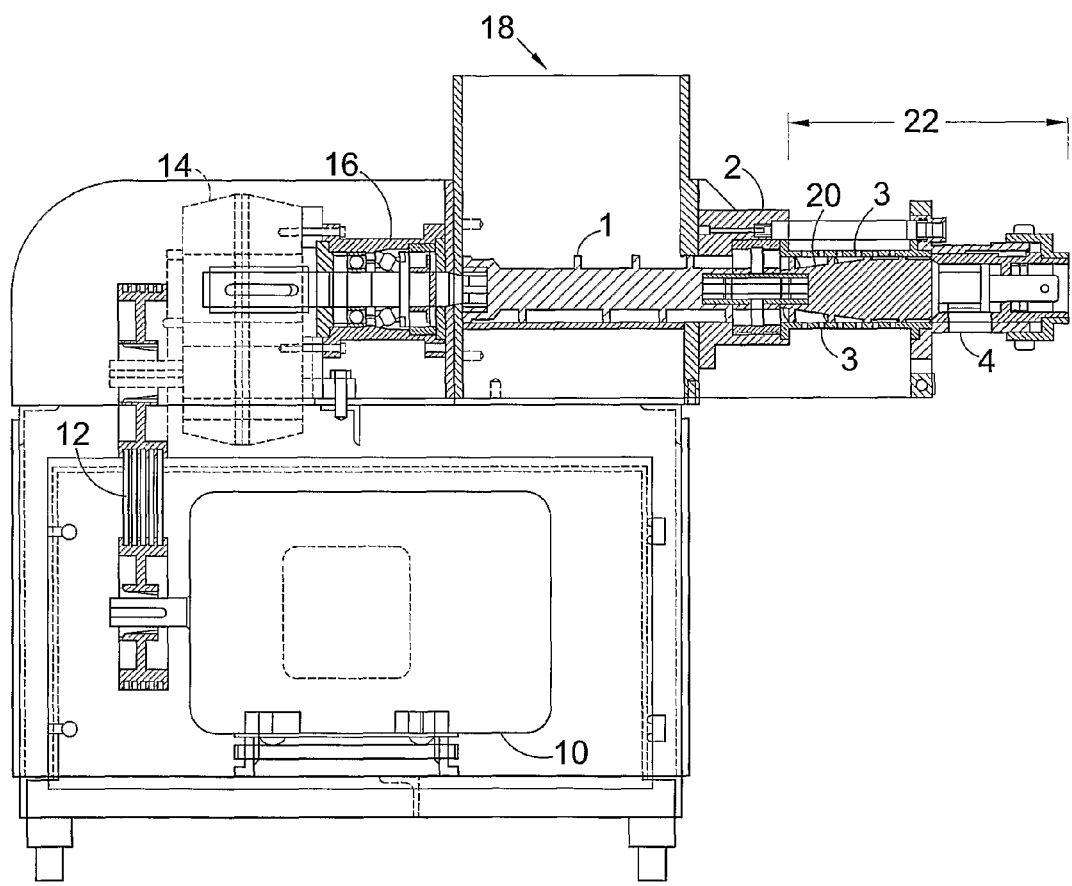
FIG. 1 depicts a schematic of a mechanical separator suitable for defatting pig rinds according to the method of the invention.

A preferred object of the present invention is the provision of a collagen product essentially from porcine sources. The inclusion of bovine collagen is not preferred but minor amounts, preferably less than 10% and particularly less than 5%, of collagens derived from sheep, poultry, birds, fish etc., may optionally be included.

The collagen properties can be varied by mixing collagen derived from young pigs (about 4 months old) and sows (female pigs about 1 year old or more). Usually, the young pig collagen comprises 10 to 100%, particularly 20 to 80% and especially 30 to 50% by weight of the mixture. Older sow material tends to be more fibrous and to increase strength in the final product.

Generally, the natural collagen comprises the whole of the skin i.e. the epidermis layer, dermis layer and subcutaneous fat layer. However, the defatting process of the invention could also be applied to skin where subcutaneous fat had already been removed. Equally, the epidermis layer could have been partially or completely removed.

Pigskin is usually obtained by killing the pig and scalding in hot water at 60° C. The bristles are then removed by singeing with a burner. The animal with the skin still in place is then cut up into joints. Pigskin is then cut from the joints to form small pieces of rind. The exact size of the rind depends on the particular joint but is typically 500-1000 $cm^2$. The largest rind tend to be about A4 paper size and come from the back of the pig. A benefit of the present invention is that rind of any size can be used.

The natural skin (particularly rind or pigskins) has to be cut into pieces of a suitable size for defatting, typically of size 1-100 $cm^2$ (e.g. 2-50 $cm^2$). This may be achieved by mincing using a rotating cutter and one or more apertured plates, or by using rotating cutters or by any other suitable cutting process.

The collagen pieces are then subjected to pressure to squeeze out fat and thereby reduce the fat content. This is advantageously done in mechanical separator such as a screw conveyor device, wherein the annular space between the screw and its casing decreases in size to apply pressure to the collagen pieces. The casing usually includes a screen out through which an impure semi-liquid fat mixture is forces by the pressurisation. The screen may be of any suitable construction, such as a mesh, apertured casing, slots or a series of abutting annular plates. Examples of suitable apparatus are described in U.S. Pat. Nos. 4,215,450, 4,340,184, 4,561,834 and 4,638,954 and are sold by Poss, Hamilton, Canada.

However, pressure may be applied in other ways such as using rollers, presses etc.

The defatted pieces are slightly reduced in size by the defatting process and are generally very irregular in shape.

The defatted collagen pieces are disintegrated to form a fibrous paste, usually by mincing following by milling. The disintegration process is carried out such as to retain the fibrous nature of the collagen and so provide strength in the final product.

If necessary, further fat removal steps may be undertaken. For example, fat may also be chemically removed by treatment with alkali, such as sodium hydroxide. Smaller amounts of fat may also be removed at other stages during the preparation of an extrudible gel. Other options include the removal of fat by solvent extraction (using acceptable food agents such as liquid carbon dioxide). Enzyme treatments are optional but are not preferred since they appear to reduce the fibrous nature of the collagen.

The fibrous collagen paste may be processed in conventional manner to produce an extrudable aqueous gel. The paste is acidified with a strong mineral acid such as hydrocholoric acid or with an organic acid such as lactic acid to swell the collagen. Alternatively, an alkaline swollen gel could be produced according to known techniques. Usually the gel comprises 94-96% water and 4-6% (typically about 5%) of collagen and other constituents by weight.

It is optional to include an alginate ester, such as an alginate glycol e.g. ethylene glycol alginate or propylene glycol alginate in the extrudable gel. This has been found to improve the strength, particularly the wet strength, of the product. Thus, improvements are found in the Burst Height Retention value and also in the Machine Direction (MD) wet tear strength. Generally, the alginate ester is present in the gel in up to 1% by weight, preferably up to 0.5% by weight (corresponding typically to up to 20%, preferably up to 10% by weight in the film). In the gel and the product the ratio of collagen to alginate ester is generally in the range 95:5 to 75:25 by weight.

Other additives including humectants such as glycerol and sorbitol together with other desired known additives (e.g. flavours, colours and spices) may be included. The humectant is preferably present in an amount of 10 to 45%, preferably 15 to 40% (e.g. 15-45%; or 10-40%) on a dry weight basis and may comprise glycerol, sorbitol or mixtures thereof. Cellulose may be included to modify the shrink tension of the casing or film. The gel may also include coagulating agents such as minor amounts of glutaraldehyde, glyoxal, liquid smoke or multivalent cation (such as aluminium) which are effective to cross-link the collagen and thereby increase its strength. Aluminium ions also waterproof the final product. This increase in strength may, however, be at the expense of reduced elasticity. The gel is then homogenised, filtered and allowed to stand prior to extrusion.

Generally, the collagen solids content of the gel on a weight basis is in the range 2 to 20%; preferably 2.5 to 7%. The collagen solids content of the final product is usually in the range 50 to 70% (typically 60%) by weight.

Extrusion of gel to form a film is generally carried out through a slot extruder and the extruded material is generally applied onto a support belt to a wet thickness in the range 0.2 to 5 mm. The extruded film may be further treated with a liquid coagulating agent such as a salt bath (for example, sodium chloride or ammonium sulphate solution), an alkali bath (for example sodium carbonate) or a glutaraldehyde solution to coagulate the film. Coagulation may also be achieved using gaseous alkali such as ammonia gas. These treatments may be applied before or after drying the product.

Extrusion to form a tubular casing can be carried out through an annular die and the extruded collagen processed in known manner to form a casing.

The collagen gel may also be extruded directly onto sausage meat or other filling in a co-extrusion apparatus.

The invention also extends to a collagen gel formed from the defatted paste and to extruded products (such as film or casing) formed from the gel. It also extends to a method of coextrusion using the gel and to coextruded products.

Embodiments of the invention will now be described by way of example only.

EXAMPLES

1) Size Reduction/Defatting

The raw material is normally fresh pork rind (singed, scalded and scraped). A typical cutting/defatting process would involve some or all of the following steps:
1. Simultaneous size reduction and preliminary fat removal using mechanical separator as described below. Removes approximately 25-40% of fat and results in pieces of rind with a collagen:fat ratio of 1:1.

Lean back rind (approximately 45 cm×20 cm) was sourced directly from a local cutting plant. Rind was cut from the meat joint at a level near to the base of the fat cones to minimise sub-cutaneous fat. Higher levels of fat in the starting material did not have a significant effect on the final product (always in range 1:1 to 2:1). Rind was removed from cold storage and fed directly into the feed hopper of a Poss mechanical separator at a rate of 1 tonne per hour in batches of 1.5 tonne. The restrictor body of the separator was adjusted manually to control the amount of material passing through the screen. With lean back rind as a starting material approximately 33% of the original batch weight could be removed, the vast majority of which was fat. A temperature rise of 16° C. was observed between rind fed into the separator and the final product. Rind pieces formed in the process varied in size typically between 2 and 42 $cm^2$ in which fat levels were reduced to 15.5% on a wet weight basis. In contrast to the original pieces of rind, residual fat was predominantly on the outer surface rather than within fat cones. The collagen content of rind pieces was in the order of 28% the remainder being made up of water. The Poss separator was able to reduce the fat content down to a ratio collagen: fat of around 1:1.

FIG. 1 is a schematic elevation of a mechanical separator suitable for defatting pieces of pig rind. The separator comprises a feed screw 1 for receiving rinds, a knife assembly 2 for cutting the rinds into pieces, a separator head 22, a perforated screen 3 through which a liquid fat mixture exits and an outlet 4 for defatted rind pieces.

In more detail, the separator comprises a drive motor 10 which drives a belt drive 12 which in turn rotates the feed screw via reduction gear 14. The feed screw 1 is rotationally mounted within a casing 16. A feed hopper 18 in the casing receives pork rind, which are conveyed by the feed screw to the knife assembly 2 which cuts the rinds into pieces. The cut pieces then pass into the separation head 22 comprising a conical separation screw 20 whose annular clearance with the perforated screen decreases in the forward direction so as to pressurise the cut pieces and force out a fat mixture through the perforated screen. The defatted pieces are carried through the separator screw and exit through the outlet 4.

2. Chemical degreasing—Residual fat can be efficiently reduced using an aqueous detergent system for example Tween 80. Defatted rind pieces are added to a vessel containing water (100-500% of rind weight). Detergent degreasing is effective at concentrations of 0.2% and greater at temperatures of between 18 and 30° C. Degreasing can be repeated to increase fat removal. Degreased rind is then rinsed 3-4 times with water (100-500% of rind weight). Rind pieces typically have collagen to fat ratio in the region 10:1 to 30:1. The final water rinse can be replaced by a treatment to improve the storage life of the de-fatted collagen e.g. buffering to pH (5 or lower) using a suitable food grade buffer, eg. a citrate buffer. Alternatively the rind pieces can be treated with alkali, such as lime (1-1%) with or without the addition of lipases (0.4-1%) and detergent (0.2+%) to further decrease fat levels, open the collagen structure and increase storage life. Rind pieces treated in this way are generally buffered to pH 4 to 6 and rinsed as described previously.

2) Production of Collagen Gel

Example: A (Pork Rind and Sowskin)

a) Fresh pork rind pieces were defatted using mechanical action and detergent cleaning methods previously described.
b) These pieces of rind were mixed with 8 mm pieces of sowskin at a ratio of 40:60 and disintegrated together; firstly with a mincing machine and then a plate mill to produce a fibrous paste.
c) This paste was blended together with a mixture of cellulose & acid to form a swollen aqueous paste of constituents:

| | |
|---|---|
| Collagen | 4.37% |
| HCl | 0.209% |
| Cellulose | 0.871% |
| Fat | 0.23% |

Final Casing Constituents on Dry Weight Basis

| Variant | % collagen | % cellulose | % glycerol | % fat | % CMC |
|---|---|---|---|---|---|
| 1 | 60.9 | 12.1 | 21 | 5 | 1.0 |
| 2 | 61.2 | 12.2 | 20.4 | 5.2 | 1.0 |
| 3 | 61.0 | 12.5 | 20 | 5.9 | 1.0 |

Final Casing Physical Attributes

| Variant | Average Cold Tensile Strength from 10 pieces | Sample standard deviation of CT from 10 pieces | Average Burst Weight from 5 pieces | Sample standard deviation of burst weight from 5 pieces |
|---|---|---|---|---|
| 1 | 2.57 Kg | 0.15 Kg | 1.04 Kg | 0.02 Kg |
| 2 | 2.51 Kg | 0.18 Kg | 0.93 Kg | 0.06 Kg |
| 3 | 2.43 Kg | 0.22 Kg | 0.82 Kg | 0.04 Kg |

Final Casing Sausage Making Attributes

Each product was stuffed using a PAL 52 vacuum filler fitted with a 15 tube and chuck assembly. To produce links of weight 47 g and nominal diameter of 26 mm and length 100 mm. In all cases the sausages were noted to be tightly filled. A standard, finely comminuted UK pork breakfast sausage recipe was used.

Surprisingly sausages prepared from new casing containing pork rind was comparable to 100% sowskin casing and 100% bovine casing when pan fried, grilled or deep fat fried.

Example: B a) Fresh pork rind pieces were defatted using mechanical action, detergent cleaning and liming with the addition of lipase as previously described.
b) These pieces of rind were mixed with 8 mm pieces of sowskin at a ratio of 40:60 and disintegrated together; firstly with a mincing machine and then a plate mill to produce a fibrous paste.
c) This paste was blended together with a mixture of cellulose & acid to form a swollen aqueous paste of constituents:

| | |
|---|---|
| Collagen | 4.57% |
| HCl | 0.206% |
| Cellulose | 1.03% |
| Fat | 0.41% |

1. This paste was homogenised through a dairy homogeniser to produce a cohesive, smooth swollen gel.
2. This gel was extruded, and simultaneously inflated with air, through an annular extruder, to a wet wall thickness of approximately 0.4 mm, onto a continuous support belt contained within an ammonia gas chamber.
3. The coagulated tubular casing was passed through a water wash bath to remove residual salt and then a further bath containing glycerol to soften it.
4. The softened casing was dried, in an inflated state, with a multi-zone drier at temperatures between 60 deg C. and 120 deg C.
5. The resultant dried tubular casing of nominal 26 mm diameter was shirred using a proprietary shirring device.
6. After shirring the casing's moisture level was increased to around 20% prior to packing with the resulting weight measured to be 2.6 g/m.

Final Casing Constituents on Dry Weight Basis (Complete Analysis not Available)

| Variant | % collagen | % cellulose | % glycerol | % fat | % CMC |
|---|---|---|---|---|---|
| 1 | 63.0 | 14.2 | 16.9 | 4.9 | 1.0 |
| 2 | 62.3 | 14.0 | 17.8 | 4.9 | 1.0 |
| 3 | 61.3 | 13.8 | 17.5 | 6.4 | 1.0 |

Final Casing Physical Attributes

| Variant | Average Cold Tensile Strength from 10 pieces | Sample standard deviation of CT from 10 pieces | Average Burst Weight from 5 pieces | Sample standard deviation of burst weight from 5 pieces |
|---|---|---|---|---|
| 1 | 3.28 Kg | 0.20 Kg | 1.17 Kg | 0.03 g |
| 2 | 3.04 Kg | 0.14 g | 1.14 Kg | 0.02 Kg |
| 3 | 2.95 Kg | 0.17 g | 1.18 Kg | 0.04 Kg |

Final Casing Sausage Making Attributes

Each product was stuffed using a PAL 52 vacuum filler fitted with a 15 tube and chuck assembly. To produce links of weight 47 g and nominal diameter of 26 mm and length 100 mm. In all cases the sausages were noted to be tightly filled. A standard, finely comminuted UK pork breakfast sausage recipe was used.

Surprisingly sausages prepared from new casing containing limed pork rind was comparable to 100% sowskin casing and 100% bovine casing when pan fried, grilled and deep fat fried. In addition the tensile properties of this material were greater than casing made from non-limed rind.

Example: C (cellulose included)

a) Fresh pork rind pieces were defatted using mechanical action and detergent cleaning methods previously described.
b) These pieces of rind were disintegrated; firstly with a mincing machine and then a plate mill to produce a fibrous paste.
c) This paste was blended together with a mixture of cellulose & acid to form a swollen aqueous paste of constituents:

| | |
|---|---|
| Collagen | 4.90% |
| HCl | 0.21% |
| Cellulose | 1.115% |
| Fat | 0.1% |

1. This paste was homogenised through a dairy homogeniser to produce a cohesive, smooth swollen gel.
2. This gel was extruded, and simultaneously inflated with air, through an annular extruder, to a wet wall thickness of approximately 0.4 mm, onto a continuous support belt contained within an ammonia gas chamber.

3. The coagulated tubular casing was passed through a water wash bath to remove residual salt and then a further bath containing glycerol to soften it.
4. The softened casing was dried, in an inflated state, with a multi-zone drier at temperatures between 60 deg C. and 120 deg C.
5. The resultant dried tubular casing of nominal 26 mm diameter was shirred using a proprietary shirring device.
6. After shirring the casing's moisture level was increased to around 20% prior to packing with the resulting weight measured to be 2.6 g/m.

Final Casing Constituents on Dry Weight Basis

| Variant | % collagen | % cellulose | % glycerol | % fat | % CMC |
|---|---|---|---|---|---|
| 1 | 61.3 | 13.9 | 20.16 | 3.64 | 1.0 |

Final Casing Physical Attributes

| Variant | Average Cold Tensile Strength from 10 pieces | Sample standard deviation of CT from 10 pieces | Average Burst Weight from 5 pieces | Sample standard deviation of burst weight from 5 pieces |
|---|---|---|---|---|
| 1 | 2.39 Kg | 0.22 Kg | .79 Kg | 0.07 Kg |

Final Casing Sausage Making Attributes

Each product was stuffed using a Handtmann VF80 vacuum filler fitted with a 15 tube and chuck assembly. To produce links of weight 47 g and nominal diameter of 26 mm and length 100 mm. In all cases the sausages were noted to be tightly filled. A standard, finely comminuted UK pork breakfast sausage recipe or premium UK pork breakfast was used.

Casing produced high degree of clarity. Cooking performance good—pan fry, grill and deep fat fry.

Example: D a) Fresh pork rind pieces were defatted using mechanical action and detergent cleaning methods previously described.
b) These pieces of rind were disintegrated; firstly with a mincing machine and then a plate mill to produce a fibrous paste.
c) This paste was blended together with acid to form a swollen aqueous paste of constituents:

| | |
|---|---|
| Collagen | 4.495% |
| HCl | 0.207% |
| Fat | 1.5% |

1. This paste was homogenised through a dairy homogeniser to produce a cohesive, smooth swollen gel.
2. This gel was extruded, and simultaneously inflated with air, through an annular extruder, to a wet wall thickness of approximately 0.4 mm, onto a continuous support belt contained within an ammonia gas chamber.
3. The coagulated tubular casing was passed through a water wash bath to remove residual salt and then a further bath containing glycerol to soften it.
4. The softened casing was dried, in an inflated state, with a multi-zone drier at temperatures between 60 deg C. and 120 deg C.
5. The resultant dried tubular casing of nominal 26 mm diameter was shirred using a proprietary shirring device.
6. After shirring the casing's moisture level was increased to around 20% prior to packing with the resulting weight measured to be 2.6 g/m.

Final Casing Constituents on Dry Weight Basis

| Variant | % collagen | % cellulose | % glycerol | % fat | % CMC |
|---|---|---|---|---|---|
| 1 | 78.0 | 0 | 15.4 | 5.6 | 1.0 |

Final Casing Physical Attributes

| Variant | Average Cold Tensile Strength from 10 pieces | Sample standard deviation of CT from 10 pieces | Average Burst Weight from 5 pieces | Sample standard deviation of burst weight from 5 pieces |
|---|---|---|---|---|
| 1 | 2.15 Kg | 0.27 Kg | .69 Kg | .05 Kg |

Final Casing Sausage Making Attributes

Each product was stuffed using a Handtmann VF80 vacuum filler fitted with a 15 tube and chuck assembly. To produce links of weight 47 g and nominal diameter of 26 mm and length 100 mm. In all cases the sausages were noted to be tightly filled. A standard, finely comminuted UK pork breakfast sausage recipe or premium UK pork breakfast was used.

Casing produced had exceptional clarity post extrusion.

Example: E (Processed Casing)

a) Fresh pork rind pieces were defatted using mechanical action and detergent cleaning methods previously described.
b) These pieces of rind were disintegrated with a milling machine to produce a fibrous paste.
c) This paste was blended together with a mixture of cellulose & acid to form a swollen aqueous paste of constituents:

| | |
|---|---|
| Collagen | 4.5% |
| HCl | 0.17% |
| Cellulose | 0.9% |
| Fat | 0.45% |
| Glutaraldehyde | 350 ppm based on collagen weight |

Final Casing Constituents on Dry Weight Basis

| % collagen | % cellulose | % glycerol | % fat + oil | % CMC |
|---|---|---|---|---|
| 59.3 | 11.8 | 18 | 9.9 | 1.0 |

Final casing Physical attributes, calibre was a nominal 23 mm stuffing size and weight was 1.7 g/m on a dry weight basis.

| Variant | Average Cold Tensile Strength from 10 pieces | Sample standard deviation of CT from 10 pieces | Average Burst Weight from 5 pieces | Sample standard deviation of burst weight from 5 pieces |
|---|---|---|---|---|
| 1 | 2.73 Kg | 0.19 Kg | 1.91 Kg | 0.17 Kg |

This casing product was stuffed using a Handtmann ALPLH machine fitted with a stepped 12 tube and chuck assembly at a speed of 400 links/minute and hanging six links per loop on a hanging unit. It produced links of weight 50 g and nominal diameter of 23.5 mm and length 120 mm. The sausages were noted to be tightly filled and stuffed without any breaks. The sausage mixture used was a typical Taiwanese style sausage. After stuffing the linked chains of sausage with loop length of 6 links were processed in accordance with 2 different regimes:

| Stage | Time | % Relative Humidity | Temp ('C.) |
|---|---|---|---|
| Regime 1: | | | |
| 1-steam | 15 | 100 | 70 |
| 2-steam | 15 | 100 | 75 |
| 3-cooling | 10 | Shower | |
| Regime 2: | | | |
| 1-drying | 10 | 50 | 60 |
| 2-steam | 15 | 100 | 70 |
| 3-steam | 15 | 100 | 75 |
| 4-cooling | 10 | Shower | |

All sausages were processed satisfactorily with no breaks, splits or falters from both processes.

These sausages were reheated on a roller-grill at a temperature of about 160 degrees Centigrade for 40 minutes and then kept warm on a roller grill at a temperature of 70 deg C. for 90 minutes.

These cooked sausages were found to be free of splits and damage, and were judged to have a desirable softer skin when compared to a commercial product well used for this application.

The invention claimed is:

1. A process for the production of a defatted collagen paste, which comprises;
    providing natural collagen from animal, mammalian, avian or fish skin;
    cutting the collagen into pieces;
    subjecting the collagen pieces to pressure in a mechanical separator to squeeze out fat and produce defatted pieces; and
    disintegrating the defatted pieces to form a fibrous paste, wherein the fibrous paste is suitable for forming casings and films for the food industry.

2. The process according to claim 1, wherein the collagen source is pig skin.

3. The process according to claim 1, wherein the collagen source is pig rind.

4. The process according to claim 2 wherein the percentage of fat in the porcine collagen paste is below 20% on a dry weight basis.

5. The process according to claim 1 wherein the ratio of collagen to fat in the paste is above 10:1.

6. The process according to claim 5 wherein the ratio is above 20:1.

7. The process according to claim 6 wherein the ratio is in the range 25:1 to 50:1.

8. The process according to claim 1, wherein the natural collagen is porcine collagen, with less than 10% derived from sheep, poultry, birds or fish.

9. The process according to claim 1, wherein the porcine collagen is derived from young pigs and sows, and comprises 20 to 80% young pig collagen.

10. The process according to claim 1, wherein the collagen is cut into pieces of size 1-100 $cm^2$.

11. The process according to claim 1, wherein the fat is squeezed out of the collagen pieces in a screw conveyor.

12. The process according to claim 1, wherein the defatted pieces are disintegrated by mincing followed by milling.

13. The process according to claim 1, which comprises further fat removal by treatment with alkali.

14. A process for the production of an extrudable collagen gel, which comprises swelling the defatted collagen paste produced according to claim 1.

15. The process according to claim 14, which further comprises the addition of an alginate glycol.

16. The process according to claim 14, which further comprises the addition of a humectant.

17. The process according to claim 14, which further comprises the addition of cellulose.

18. The process according to claim 14, which further comprises a coagulating agent.

19. The process according to claim 14 wherein the collagen solids content of the gel on a weight basis is in the range 2 to 20%.

* * * * *